(12) United States Patent
Gyollai et al.

(10) Patent No.: US 7,452,991 B2
(45) Date of Patent: Nov. 18, 2008

(54) AZTREONAM β POLYMORPH WITH VERY LOW RESIDUAL SOLVENT CONTENT

(75) Inventors: Viktor Gyollai, Debrecen (HU); Csaba Szabo, Debrecen (HU); Claude Singer, Kfar Saba (IL); Ehud Amir, Ramat-Aviv (IL)

(73) Assignee: Teva Gyógyszergyár Zártkörüen Müködö Részvénytársaság, Debrecen (HU)

( * ) Notice: Subject to any disclaimer, the term of this patent is extended or adjusted under 35 U.S.C. 154(b) by 96 days.

(21) Appl. No.: 10/847,123

(22) Filed: May 17, 2004

(65) Prior Publication Data

US 2005/0014739 A1    Jan. 20, 2005

Related U.S. Application Data

(60) Provisional application No. 60/470,788, filed on May 15, 2003.

(51) Int. Cl.
C07D 205/085 (2006.01)
(52) U.S. Cl. .................................................. 540/355
(58) Field of Classification Search ........................ None
See application file for complete search history.

(56) References Cited

U.S. PATENT DOCUMENTS

| | | |
|---|---|---|
| 4,529,698 A | 7/1985 | Sykes et al. |
| 4,652,651 A | 3/1987 | Furlenmeier et al. |
| 4,775,670 A | 10/1988 | Sykes et al. |
| 4,826,973 A | 5/1989 | Anderson et al. |
| 4,923,998 A | 5/1990 | Takaya et al. |
| 4,946,838 A | 8/1990 | Floyd et al. |
| 5,194,604 A | 3/1993 | Denzel et al. |
| 5,254,681 A | 10/1993 | Guanti et al. |
| 2004/0062721 A1 | 4/2004 | Montgomery |
| 2004/0063682 A1 | 4/2004 | Gyollai et al. |
| 2005/0032775 A1 | 2/2005 | Gyollai et al. |
| 2006/0276640 A1* | 12/2006 | Fimognari .................. 540/355 |

FOREIGN PATENT DOCUMENTS

| | | |
|---|---|---|
| EP | 0 070 024 A1 | 1/1983 |
| EP | 0 297 580 A1 | 1/1989 |
| PL | 165 700 B1 | 8/1993 |
| WO | WO 02/051356 A2 | 7/2002 |
| WO | WO 03/018578 A1 | 3/2003 |
| WO | WO 2004/052333 A1 | 6/2004 |

* cited by examiner

*Primary Examiner*—Mark L Berch
(74) *Attorney, Agent, or Firm*—Kenyon & Kenyon LLP

(57) ABSTRACT

The invention relates to the β polymorph of Aztreonam, which contains less than 2.5% by weight residual solvent and to a process of making said polymorph. In the process of the invention, a polymorph of Aztreonam is dissolved in an absolute $C_{1-6}$ alcohol in the presence of a base to form a solution, an acid is added to the solution, and the solution is stirred efficiently.

46 Claims, No Drawings

AZTREONAM β POLYMORPH WITH VERY LOW RESIDUAL SOLVENT CONTENT

CROSS-REFERENCE TO RELATED APPLICATIONS

This application claims the benefit of U.S. Provisional Application Ser. No. 60/470,788, filed May 15, 2003, the content of which is incorporated herein.

FIELD OF THE INVENTION

The invention relates to a crystalline, anhydrous β polymorph of [3S-[3α(Z),4β]]-3-[[(2-amino-4-thiazolyl)[(1-carboxy-1-methylethoxy)imino]acetyl]amino]-4-methyl-2-oxo-1-azetidine-sulfonic acid (Aztreonam), having less than 2.5% by weight residual solvent and to a method for making said polymorph.

BACKGROUND OF THE INVENTION

U.S. Pat. No. 4,946,838, assigned to E.R. Squibb & Sons, Inc., discloses a crystalline anhydrous form of the antibacterial agent, [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid (Aztreonam). This crystalline, anhydrous form is designated as the β polymorph. According to the '838 patent, its main advantages compared to the α-polymorph are higher thermal stability, flowability and lower hygroscopicity. The new polymorph is characterized by X-ray powder diffraction.

Polymorph β can be obtained by crystallization of α-Aztreonam from anhydrous solvents such as alcohols, most preferably ethanol or by the precipitation of the Aztreonam salt with an organic amine in the presence of HCl. (see U.S. Pat. No. 4,826,973). U.S. Pat. No. 4,826,973, assigned to E. R. Squibb & Sons, Inc., discloses, in Table II, that the crystals of the β-form contain 0-1% water and 2.5% ethanol. This relatively high solvent content makes this form unsuitable for pharmaceutical formulations.

SUMMARY OF THE INVENTION

The invention provides a crystalline, anhydrous β polymorph of [3S-[3α(Z),4β]]-3-[[(2-amino-4-thiazolyl)[(1-carboxy-1-methylethoxy)imino]acetyl]amino]-4-methyl-2-oxo-1-azetidine-sulfonic acid (Aztreonam), having less than 2.5% by weight residual solvent. Preferably, the β polymorph of Aztreonam has less than 1% by weight residual solvent. Most preferably, the β polymorph of Aztreonam has less than 0.5% by weight residual solvent.

The invention further provides a process for preparing a crystalline, anhydrous β polymorph of Aztreonam, which entails dissolving Aztreonam in an organic solvent at a temperature of between about −60° C. to about 5° C. in the presence of a base to form a clear solution, and adding acid to the solution while stirring efficiently until a precipitate is obtained. Preferably, the solution is seeded with β Aztreonam, while the efficient stirring continues. Preferably the precipitate is reslurried in ethanol.

Preferably, the obtained β Aztreonam polymorph contains less than 2.5% by weight residual solvent. Most preferably, the β polymorph of Aztreonam has less than 1% by weight residual solvent. Most preferably, the β polymorph of Aztreonam has less than 0.5% by weight residual solvent.

DETAILED DESCRIPTION OF THE INVENTION

The invention provides a crystalline, anhydrous β polymorph of Aztreonam, having less than 2.5% by weight residual solvent. Preferably, the β polymorph of Aztreonam has less than 1% by weight residual solvent. Most preferably, the β polymorph of Aztreonam has less than 0.5% by weight residual solvent. The term "solvent" means organic solvent, such as a $C_{1-6}$ alcohol, preferably absolute $C_{1-6}$ alcohol, e.g., ethanol, methanol, isopropanol, etc. Preferably the organic solvent is absolute ethanol. The solvent may be hydrated or anhydrous.

The term "residual solvent" refers to the solvent used in the reaction.

Applicants observed that the crystallization of β-Aztreonam (as described in the patents mentioned above) is different from the "normal" crystallization process. The precipitation of its crystals starts spontaneously in the coincidence of two independent factors. One factor is the concentration of Aztreonam in the solution, the other is the water content of the solution. The former should be high enough and the latter should be low enough in order to induce crystallization of this polymorph. These two parameters are gradually and uncontrollably approaching their limit-value parallel with the dissolution of crude Aztreonam. The precipitation is usually very quick after reaching this critical point. The effect of temperature on crystallization was also observed. In particular, at higher temperature precipitation becomes considerably faster. Because of this rapid growth of crystals, the formation of agglomerates occurs spontaneously as well. The agglomerates are suspected of being responsible for the high solvent content of this polymorph.

Based on these observations, Applicants aimed to modify the crystallization of β-Aztreonam, i.e., to decrease the rate of precipitation and thus hinder the formation of agglomerates. The precipitation rate was successfully decreased by using a low crystallization temperature, preferably 5° C. or less. When temperatures of 5° C. or lower are used, crystallization is slow enough to obtain a low residual solvent content in the final product. The time of crystallization is typically 16-24 h at 5° C. and it is even longer at lower temperatures.

The other important factor that affects the residual solvent content is the rate of stirring. In the absence of stirring or using slow and inefficient stirring, a high solvent content was detected in the product. For example, efficient stirring in a 1 L glass reactor is achieved at a rate of at least 500 rpm (more preferably 700 rpm) using a large diameter paddle stirrer.

The β polymorph of Aztreonam made according to the invention, contained less than 0.5% solvent, as recommended by the ICH guidelines. Its water content is typically 0.5%. In summary, the good drying ability is attributed to the low temperature of crystallization and the efficient stirring which enable the slow growth of crystals (crystallization completes in 16-24 h). These three factors result in the lack of agglomerates, which are believed to be responsible for trapping solvent molecules.

The β polymorph of Aztreonam having less than 2.5% solvent, may be made by dissolving Aztreonam, preferably a polymorph of Aztreonam, most preferably the α polymorph, in an organic solvent at a temperature of between about −60° C. to about 5° C., preferably from about −40° C. to about 5° C., more preferably from about −25° C. to about 5° C., and most preferably from about −5° C. to about 5° C., in the presence of a base to form a clear solution, and adding acid while efficiently stirring the solution until a precipitate is obtained. Preferably, the solution is seeded with β Aztreonam while the efficient stirring is continued. Preferably, the precipitate is reslurried in ethanol.

The phrase "efficient stirring" means turbulent stirring such that the peripheral velocity of the stirrer is preferably 25 m/s or greater, more preferably 100 m/s or greater, and most preferably 400 m/s or greater. The stirring rate depends on the reactor volume. For example, at least 500 rpm is turbulent stirring for a reactor volume of 1 liter.

The starting material may be any known polymorph of Aztreonam such as the α, β, δ or γ aztreonam polymorphs.

Preferably, the organic solvent used to dissolve the polymorph of Aztreonam is a $C_{1-6}$ alcohol, preferably absolute $C_{1-6}$ alcohol, such as ethanol, methanol, isopropanol etc., most preferably, the solvent is absolute ethanol.

The base used in the process is selected from the group consisting of triethylamine, n-butylamine and 2,4,6-trimethyl pyridine. Preferably, the base is gaseous or aqueous triethylamine. The base is preferably added in an amount of 1.1-1.2 moles per mole of the α polymorph of Aztreonam.

The acid used in the process is preferably concentrated hydrochloric acid. It is preferably added in an amount sufficient to adjust the pH of the solution to between about 1.8-3.2, more preferably to between about 2.2-2.8.

After the acid is added, the solution is seeded with ~1% β-Aztreonam with efficient stirring for a time sufficient to precipitate the β polymorph of Aztreonam.

EXAMPLES

Example 1

In a glass reactor, 18 g α-Aztreonam is added to a mixture of 240 ml absolute ethanol and 11.5 ml ethanolic ammonia (3.65 M, 1.2 equiv.) at 0° C. with stirring. After 10-30 min the insoluble material is filtered off (filter is washed with 30 ml chilled absolute ethanol) and the solution is acidified with 3.6 ml aq. HCl (37%, 1.22 equiv.). The solution is immediately seeded with 0.18 g β-Aztreonam and the hazy solution is stirred efficiently (500 rpm) overnight at this temperature. After filtration the product is dried at 38° C. in an air-circulating oven. Yield: 13.7 g; Residual ethanol: 0.95%

Example 2

In a glass reactor, 18 g α-Aztreonam is added to a mixture of 240 ml absolute ethanol and 11.5 ml ethanolic ammonia (3.65 M, 1.2 equiv.) at 0° C. with stirring. After 10-30 min the insoluble material is filtered off (filter is washed with 30 ml chilled absolute ethanol) and the solution is acidified with ethanolic HCl (3.6 M) to pH 2.4. The solution is immediately seeded with 0.18 g β-Aztreonam and the hazy solution is stirred efficiently (500 rpm) overnight at this temperature. After filtration the product is dried at 38° C. in an air-circulating oven. Yield: 14.5 g; Residual ethanol: 0.78%

Example 3

In a glass reactor, 75.6 g α-Aztreonam is added to a mixture of 1050 ml absolute ethanol and 30 ml triethylamine (1.2 equiv.) at 0° C. with stirring. After 10-30 min the insoluble material is filtered off and the solution is acidified with ethanolic HCl (3.6 M) to pH 2.0. The solution is immediately seeded with 0.8 g β-Aztreonam and the hazy solution is stirred efficiently (600 rpm) overnight at this temperature. After filtration the product is dried at 38° C. in an air-circulating oven. Yield: 58.7; Residual ethanol: 0.18%

Example 4

8.6 kg Aztreonam crude dry, 115 L ethanol absolute and 5.5 L ethanolic ammonia was charged at 0° C. into a 400-liter reactor. The solution was stirred at 0° C. for 1 hr. The solution was acidified to pH=2.9 with 1.5 L HCl 32% and seeded. The stirring was maintained for 16 hours at 0° C. The suspension was filtrated and washed with absolute ethanol. 11.9 kg of wet material was obtained. The wet material (11.9-Kg) was reslurried twice with 95% ethanol at 45° C. in a 160-liter reactor. 6.4 Kg of wet material was obtained. The solid was dried in a vacuum oven. The polymorph of the dry sample was the β polymorph of Aztreonam containing 0.496% residual ethanol.

What is claimed is:

1. Crystalline, anhydrous β polymorph of Aztreonam having about 0.5% or less by weight of residual solvent.

2. The crystalline, anhydrous β polymorph of Aztreonam of claim 1, containing residual solvent, wherein the residual solvent is present in an amount of about 0.5% or less by weight.

3. The crystalline, anhydrous β polymorph of Aztreonam of claim 2, containing residual solvent, wherein the residual solvent is present in an amount of about 0.18% by weight.

4. A method for making the crystalline, anhydrous β polymorph of Aztreonam, comprising:
(a) dissolving a polymorph of Aztreonam in an absolute $C_{1-6}$ alcohol at a temperature of between about −60° C. to about 5° C. in the presence of a base to form a clear solution;
(b) adding acid to the solution formed in (a);
(c) stirring the solution efficiently; and
(d) recovering the β polymorph of Aztreonam.

5. The process of claim 4, wherein the obtained β polymorph of Aztreonam has less than 2.5% by weight residual solvent.

6. The process of claim 5, wherein the obtained β polymorph of Aztreonam has less than 1% by weight residual solvent.

7. The process of claim 6, wherein the obtained β polymorph of Aztreonam has less than 0.5% by weight residual solvent.

8. The process of claim 4, further comprising seeding the solution with the β polymorph of Aztreonam prior to step (d).

9. The process of claim 4, further comprising forming a slurry with ethanol prior to step (d).

10. The method of claim 4, wherein the temperature in (a) is between about −40° C. to about 5° C.

11. The method of claim 10, wherein the temperature in (a) is between about −25° C. to about 5° C.

12. The method of claim 11, wherein the temperature in (a) is between about −5° C. to about 5° C.

13. The method of claim 4, wherein the base is selected from the group consisting of triethylamine, n-butylamine and 2,4,6-trimethyl pyridine.

14. The method of claim 13, wherein the base is triethylamine.

15. The method of claim 4, wherein said absolute $C_{1-6}$ alcohol is absolute ethanol.

16. The method of claim 4, wherein said polymorph of Aztreonam is the α polymorph.

17. The method of claim 4, wherein the base in (a) is added in an amount of about 1.1 to about 1.2 moles per mole of the α polymorph.

18. The method of claim 4, wherein the acid in (b) is concentrated hydrochloric acid.

19. The method of claim 18, wherein the hydrochloric acid is added in an amount sufficient to adjust the pH of the solution to between about 1.8 to about 3.2.

20. The method of claim 19, wherein the hydrochloric acid is added in an amount sufficient to adjust the pH of the solution to between about 2.2 to about 2.8.

21. The method of claim 8, wherein the β polymorph of Aztreonam is added in an amount of about 1% by weight.

22. The method of claim 4, wherein the stirring in (c) is such that the peripheral velocity of the stirrer is 25 m/s or greater.

23. The method of claim 22, wherein the stirring in (c) is such that the peripheral velocity of the stirrer is 100 m/s or greater.

24. The method of claim 23, wherein the stirring in (c) is such that the peripheral velocity of the stirrer is 400 m/s or greater.

25. The process of claim 4, wherein the solution in (c) is efficiently stirred for about 16 to about 24 hours.

26. A method for making the crystalline, anhydrous β polymorph of Aztreonam having less than 2.5% by weight residual solvent, comprising
  (a) dissolving a polymorph of Aztreonam in an absolute $C_{1-6}$ alcohol, in the presence of a base, at a temperature sufficient to achieve crystallization of the β polymorph within about 16 to about 24 hours;
  (b) adding acid to the solution formed in (a);
  (c) seeding the solution with the β polymorph of Aztreonam; and
  (d) stirring the solution efficiently for a time sufficient to precipitate the β polymorph of Aztreonam.

27. The method of claim 26, wherein the temperature in (a) is about 0° C. or less.

28. The method of claim 26, wherein the crystalline, anhydrous β polymorph of Aztreonam has less than 1% by weight residual solvent.

29. The method of claim 28, wherein the crystalline, anhydrous β polymorph of Aztreonam has less than 0.5% by weight residual solvent.

30. A method for making the crystalline, anhydrous β polymorph of Aztreonam,
  comprising:
  (a) dissolving a polymorph of Aztreonam in an absolute $C_{1-6}$ alcohol at a temperature of between about −60° C. to about 5° C. in the presence of a base to form a clear solution;
  (b) adding acid to the solution formed in (a);
  (c) stirring the solution efficiently;
  (d) seeding with the β polymorph of Aztreonam;
  (e) forming a slurry with ethanol; and
  (d) recovering the β polymorph of Aztreonam.

31. Crystalline β polymorph of Aztreonam, having about 0.5% or less by weight of residual solvent, prepared by the process of claim 4.

32. Crystalline β polymorph of Aztreonam, having about 0.5% or less by weight of residual solvent, prepared by the process of claim 8.

33. Crystalline β polymorph of Aztreonam, having 1% or less by weight of residual ethanol, prepared by the process of claim 9.

34. Crystalline β polymorph of Aztreonam, having about 0.5% or less by weight of residual solvent, prepared by the process of claim 26.

35. Crystalline β polymorph of Aztreonam, having 1% or less by weight of residual ethanol, prepared by the process of claim 30.

36. The crystalline, anhydrous β polymorph of Aztreonam of claim 35, wherein the residual ethanol is present in an amount of about 0.5% or less by weight.

37. The crystalline, anhydrous β polymorph of Aztreonam of claim 35, wherein the residual ethanol is present in an amount of about 0.18% by weight.

38. The crystalline, anhydrous β polymorph of Aztreonam of claim 33, wherein the residual ethanol is present in an amount of about 0.5% or less by weight.

39. The crystalline, anhydrous β polymorph of Aztreonam of claim 33, wherein the residual ethanol is present in an amount of about 0.18% by weight.

40. The crystalline, anhydrous β polymorph of Aztreonam of claim 31, wherein the residual solvent is present in an amount of about 0.18% by weight.

41. The crystalline, anhydrous β polymorph of Aztreonam of claim 32, wherein the residual solvent is present in an amount of about 0.18% by weight.

42. The crystalline, anhydrous β polymorph of Aztreonam of claim 34, wherein the residual solvent is present in an amount of about 0.18% by weight.

43. Crystalline, anhydrous β polymorph of Aztreonam, containing ethanol, wherein the ethanol is present in an amount of 1% or less by weight.

44. The crystalline, anhydrous β polymorph of Aztreonam of claim 43, wherein the ethanol is present in an amount of about 0.5% or less by weight.

45. The crystalline, anhydrous β polymorph of Aztreonam of claim 43, wherein the ethanol is present in an amount of about 0.18% by weight.

46. Crystalline, anhydrous β polymorph of Aztreonam, containing methanol, wherein the methanol is present in an amount of about 0.5% or less by weight.

* * * * *

UNITED STATES PATENT AND TRADEMARK OFFICE
CERTIFICATE OF CORRECTION

PATENT NO. : 7,452,991 B2
APPLICATION NO. : 10/847123
DATED : November 18, 2008
INVENTOR(S) : Gyollai et al.

It is certified that error appears in the above-identified patent and that said Letters Patent is hereby corrected as shown below:

Column 4
Line 34, change "process" to --method--
Line 37, change "process" to --method--
Line 40, change "process" to --method--
Line 43, change "process" to --method--
Line 45, change "process" to --method--

Column 5
Line 18, change "process" to --method--

Signed and Sealed this

Twenty-fifth Day of August, 2009

David J. Kappos
*Director of the United States Patent and Trademark Office*